United States Patent [19]
Belden

[11] Patent Number: 5,409,455
[45] Date of Patent: Apr. 25, 1995

[54] VASCULAR NAVIGATION AND VISUALIZATION ASSIST DEVICE

[75] Inventor: Elisabeth L. Belden, Plymouth, Minn.

[73] Assignee: Scimed Life Systems, Inc., Maple Grove, Minn.

[21] Appl. No.: 89,003

[22] Filed: Jul. 9, 1993

[51] Int. Cl.⁶ ............................................. A61M 3/00
[52] U.S. Cl. ................................... 604/43; 604/902; 604/283
[58] Field of Search ............... 604/902, 280, 283, 27, 604/31-35, 43

[56] References Cited

U.S. PATENT DOCUMENTS

| | | |
|---|---|---|
| 3,196,876 | 7/1965 | Miller . |
| 4,072,146 | 2/1978 | Howes . |
| 4,437,857 | 3/1984 | Goldstein et al. . |
| 4,551,292 | 11/1985 | Fletcher et al. ................ 604/280 |
| 4,551,292 | 11/1985 | Fletcher et al. . |
| 4,554,929 | 11/1985 | Samson et al. . |
| 4,571,240 | 2/1986 | Samson et al. . |
| 4,657,024 | 4/1987 | Coneys ............................. 604/280 |
| 4,732,154 | 3/1988 | Shiber . |
| 4,739,768 | 4/1988 | Engelson . |
| 4,819,751 | 4/1989 | Shimada et al. . |
| 4,838,269 | 6/1989 | Robinson et al. . |
| 4,898,575 | 2/1990 | Fischell et al. . |
| 4,928,693 | 5/1990 | Goodin et al. . |
| 4,932,413 | 6/1990 | Shockey et al. . |
| 4,938,220 | 7/1990 | Mueller, Jr. . |
| 4,955,862 | 9/1990 | Sepetka . |
| 4,968,306 | 11/1990 | Huss et al. . |
| 4,976,689 | 12/1990 | Buchbinder et al. . |
| 5,021,044 | 6/1991 | Sharkawy . |
| 5,102,390 | 4/1992 | Crittenden et al. . |
| 5,120,323 | 6/1992 | Shockey et al. ................ 604/282 |
| 5,120,323 | 6/1992 | Shockey et al. . |
| 5,131,406 | 7/1992 | Kaltenbach . |
| 5,147,315 | 9/1992 | Weber . |
| 5,156,596 | 10/1992 | Balbierz et al. . |
| 5,163,927 | 11/1992 | Woker et al. . |
| 5,171,305 | 12/1992 | Schickling et al. . |
| 5,178,608 | 1/1993 | Winters . |
| 5,207,648 | 5/1993 | Gross ............................... 604/283 |
| 5,254,107 | 10/1993 | Soltesz ............................. 604/280 |

FOREIGN PATENT DOCUMENTS

0535874A1 4/1993 European Pat. Off. .

OTHER PUBLICATIONS

"Subselective Diagnostic and Interventional Arteriography Using a Simple Coaxial Catheter System," by Patrick C. Freeny et al., CardioVascular and Interventional Radiology, pp. 209-213, 1984.

Primary Examiner—Jerome L. Kruter
Attorney, Agent, or Firm—Robert E. Atkinson

[57] ABSTRACT

An intravascular device to assist in the visualization of intravascular lumens and the navigation of guide members, the device including two elongate coaxial tubes which define a central lumen and an annular lumen. A manifold is coupled to the proximal end of the two tubes and includes a first port connected to the central lumen and a second port in fluid communication with the annular lumen. The central lumen and the annular lumen are fluidly independent at the proximal end and are open to the vasculature at the distal end. The coaxial tubes engage each other at the distal end to limit longitudinal movement therebetween.

1 Claim, 5 Drawing Sheets

VASCULAR NAVIGATION AND VISUALIZATION ASSIST DEVICE

FIELD OF THE INVENTION

The present invention relates to the construction and use of intravascular devices. Specifically, the present invention relates to the construction and use of intravascular devices facilitating the navigation of guide members along vascular pathways and the visualization of vascular pathways.

BACKGROUND OF THE INVENTION

Vascular occlusions are now commonly diagnosed and treated by nonsurgical procedures. Coronary artery disease, for example, is a disease resulting in the full or partial occlusion of a coronary artery and is frequently treated by a nonsurgical procedure called percutaneous translumenal coronary angioplasty (PTCA). Peripheral translumenal angioplasty (PTA) is a similar nonsurgical procedure used to provide therapy to occlusions in the peripheral arteries. Other nonsurgical translumenal procedures such as atherectomy and laser ablation can be implemented to provide therapy to vascular occlusions occurring in the coronary arteries, peripheral arteries, cerebral arteries, and several other vascular sites.

Most nonsurgical translumenal procedures require the use of some type of guide member because the access point and the therapy site are a significant distance apart. The guide member can be used to guide a therapeutic device from the access point and along a vascular path leading to the site where therapy is to be provided.

Vascular paths are often long and tortuous and are thus sometimes difficult to navigate. Furthermore, vascular occlusions can be difficult to cross with a guide member due to the restricted through lumen. Vascular occlusions also inhibit fluid flow and thus the vascular path adjacent to and distal to the occlusion are difficult or impossible to visualize clearly with contrast media injections. The need to use guide members for nonsurgical translumenal procedures in combination with the difficulties in navigating and visualizing tortuous occluded vascular pathways defines the need to provide a device to assist in the navigation and visualization of vascular pathways.

Several intravascular devices have been described which purport to aid the advancement of guide wires and the like, and/or allow for the injection of fluids. Engleson U.S. Pat. No. 4,739,768 describes a single lumen device used to track a guide wire from an access site to an internal tissue along a tortuous path. The device can also be used to deliver an injectable fluid at a tissue site. Shockey et al U.S. Pat No. 5,120,323 describes a guide catheter system including two single lumen guide catheters. A working catheter can be passed through the inner catheter and fluids can be perfused between the inner catheter and the outer catheter. Kaltenbach U.S. Pat. No. 5,131,406 describes a guide which can be introduced into a narrow passage in a human body, such as into a narrow blood vessel in a human heart. Sharkawy U.S. Pat. No. 5,021,044 describes a multilumen vascular catheter for the delivery of therapeutic fluids to a patient's blood vessel.

SUMMARY OF THE INVENTION

The structure and function of the present invention renders several advantages over the prior art devices. The structure includes two elongate coaxial tubes which define a central lumen and an annular lumen. A manifold is coupled to the proximal end of the two tubes and includes a first port connected to the central lumen and a second port in fluid communication with the annular lumen. The central lumen and the annular lumen are fluidly independent at the proximal end, and are open at the distal end.

Alternatively, the structure may include a single elongate tube with two independent lumens defined therethrough. A similar manifold is used and provides two ports for access to each lumen. Again, the lumens are fluidly independent at the proximal end and are open at the distal end.

The present invention can be used as an ancillary tool, a diagnostic tool, and a therapeutic tool. As an ancillary tool, it facilitates the advancement and manipulation of a guide member. As a diagnostic tool, it facilitates the visualization of vascular pathways, occlusions, etc. As a therapeutic tool, the present invention allows for the infusion of therapeutic drugs, such as fluids that utilize proteases or enzymes to break down atherosclerotic tissue and thrombus.

Those skilled in the art will be able to practice the invention with reference to the following drawings and detailed description of a preferred embodiment.

DESCRIPTION OF THE DRAWINGS

The following drawings are referenced in the text of the detailed description of the invention. Several figures are presented in which like numerals in different figures refer to identical parts.

DETAILED DESCRIPTION OF THE INVENTION

Figure 1:
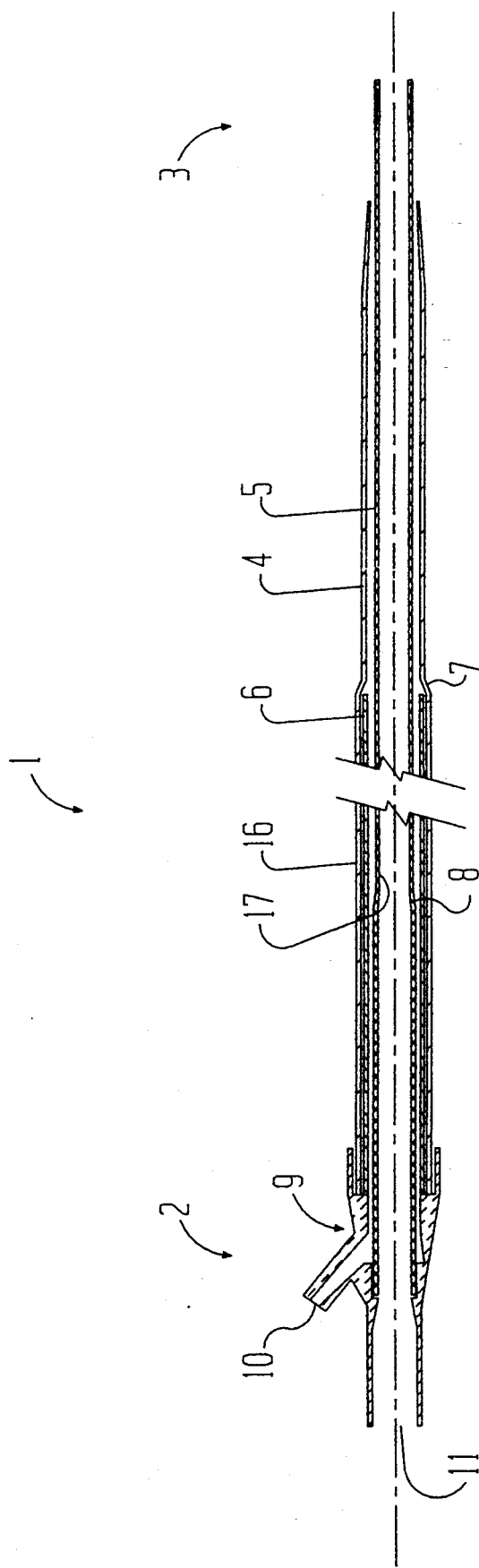
FIG. 1 is a cross-sectioned side view of the preferred embodiment of the present invention.

Referring to FIG. 1, the device (1) is designed to extend partially into the vasculature of the human body, and extend partially outside the body. Therefore, it must be of sufficient length to allow for external manipulation by the treating physician and to extend from the vascular access point along the vascular pathway to the therapy site. The preferable length of the device (1) for treating coronary arteries from the femoral artery access point is about 125–140 cm. The device (1) must also be of sufficient profile to fit into any vascular access tubes such as an introducer sheath or a guide catheter. The preferable outer profile of the device (1) for treating coronary arteries from the femoral artery access point is about 0.048–0.052 inch at the proximal portion of the device (2) and about 0.038–0.044 inch at the distal end of the device (3). The profile at the distal end of the device (3) is smaller than the profile at the proximal end of the device (2) so as to provide for more flexibility where the device enters tortuous vasculature and more stiffness where the device is being manipulated. Also, the distal portion of the device (3) must be of small enough profile to fit into small vessels and occluded vessels.

The device (1) can be coated on its external surface (16) with a lubricious coating which reduces the friction between the device and any contacting surfaces such as a guide catheter or the inner walls of the vasculature. Acceptable coatings include silicone coatings, hydrophylic coatings, and polytetrafluoroethylene (PTFE) coatings. Preferably, the device is coated on the portion extending inside the body, and not on the portion extending outside the body. The reduced friction on the portion of the device inside the body makes the device easier to manipulate while not making the device difficult to handle.

Continuing to refer to FIG. 1, the device (1) includes an inner tube (5) extending from the proximal end of the device (2) to the distal end of the device (3). The inner tube (5) is preferably made of polyethylene (PE) because of its flexibility, low friction, biocompatibility characteristics, relatively low cost, and ease of manufacture. Other suitable materials meeting the physical requirements and the biocompatibility requirements, such as polytetrafluoroethylene (PTFF.), polypropylene, or polyester may be used as well. The inner extends from the proximal end (2) to an inner mid-shaft taper (8). The length of this portion is about 90–95 cm with an inside diameter of about 0.0213–0.0223 inch and an outside diameter of about 0.0273–0.0283 inch. The inner mid-shaft taper (8) and the distal dimensions of the inner tube (5) are formed by pulling the inner tube (5) through a heated die while disposed about a mandrel. The length of the inner tube (5) extending from the inner mid-shaft taper (8) to the distal end (3) is about 40–45 cm with an inside diameter of about 0.0190–0.0200 inch and an outside diameter of about 0.0243–0.0253 inch.

Continuing to refer to FIG. 1, the device (1) includes an outer tube (4) extending from the proximal end of the device (2) to the distal end of the device (3) and is coaxially positioned about the inner tube (5). The outer tube (4) is preferably made from the same material options as the inner tube (5). The outer extends from the proximal end (2) to an outer mid-shaft taper (7). The length of this portion is about 95–100 cm with an inside diameter of about 0.042–0.046 inch and an outside diameter of about 0.048–0.052 inch. The outer mid-shaft taper (7) and the distal dimensions of the outer tube (4) are formed by pulling the outer tube (4) through a heated die while disposed about a mandrel. The length of the outer tube (4) extending from the outer mid shaft taper (7) to the distal end (3) is about 30–40 cm with an inside diameter of about 0.034–0.038 inch, an outside diameter of about 0.040–0.044 inch, and a wall thickness of about 0.003 inch.

The stiffening tube (6) as seen in FIG. 1 is coaxially positioned between the inner tube (5) and the outer tube (4) and is preferably made of polycarbonate which is relatively stiffer than polyethylene. The stifferting tube may be made of any suitable polymer with the appropriate rigidity such as polyimide. The stiffening tube extends from the proximal portion of the device (2) to the outer mid-shaft taper (7) for a length of about 95–100 cm and is dimensioned to slide within the necked outer shaft. The dimensions of the stiffening tube (6) are an inside diameter of 0.034–.038 inch, an outside diameter of about 0.040–0.044 inch, and a wall thickness of about 0.003 inch.

The dimensions of the inner tube (5), the outer tube (4) and the stiffening tube (6) may vary depending on the fluid flow, guide member compatibility, flexibility, trackability, and pushability characteristics desired. The dimensions given are the preferred dimensions for a device designed for the coronary arteries accessed from the femoral artery in the groin. Specifically, the dimensions are adapted for use in combination with a guide member with an outside diameter of about 0.018 inch or less. The device (1) can be dimensioned for other vascular access points and therapy sites as well as different guide members.

Figure 2:
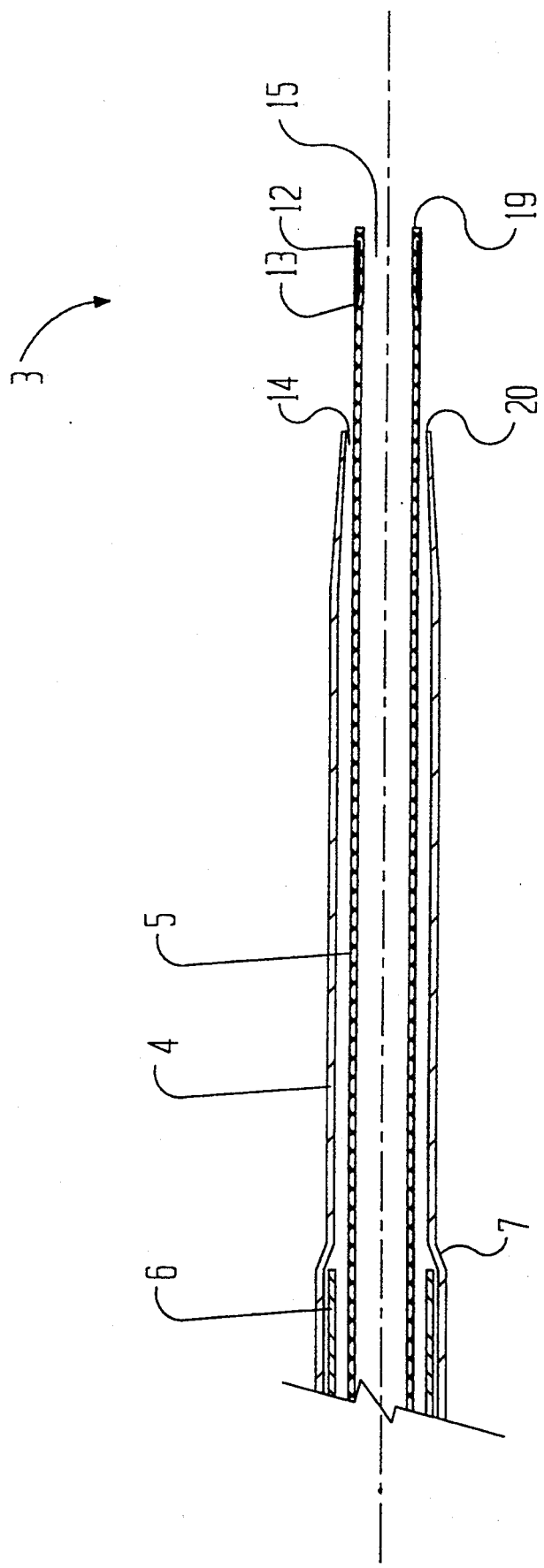
FIG. 2 is a detailed cross-sectioned side view of the distal portion of the preferred embodiment of the present invention.

Referring now to FIG. 2, the inner tube (5) terminates distally at a distal tip (19) including a coaxially mounted marker band (12) adhesively secured by a suitable flexible adhesive potting (13) such as urethane. The marker band (12) is loaded onto the inner tube (5) by necking to a sufficient outside diameter to slide the marker band thereon. The necking is accomplished by a similar process as used the make the mid-shaft tapers (7,8). The resulting dimensions of the necked inner tube adjacent the marker band (12) are an inside diameter of about 0.0185–0.0195 inch, an outside diameter of about 0.0205–0.0215 inch, and a length of 1–2 mm. The distal tip of the inner tube (19) can be pushed into a heated die in order to bulk up material just distal to the marker band (12). This creates a ledge on either side of the marker band which serves to prevent the marker band from sliding along the inner tube. The distal tip of the inner tube (19) extends a total of about 1.5–3.0 mm beyond the distal tip of the outer tube (20). The adhesive potting (13) provides a smooth transition over the marker band (12).

The marker band (12) may be made of any suitable radio opaque material such as gold, platinum, tungsten, and any alloys thereof. For example, the marker band (12) may be made of a platinum alloy consisting of 90% platinum and 10% iridium, with a length of about 0.020 inch, an inside diameter of about 0.0215–0.0225 inch and an outside diameter of about 0.0255–0.0265 inch. Locating the marker band (12) at the very distal end of the device (1) facilitates locating the most distal point at which the vascular path has been navigated which in turn indicates the true location of the most distal tip of the device (19) with respect to distal end of a guide member (not shown).

Continuing to refer to FIG. 2, the distal end of the outer tube (20) is necked down to provide a smooth transition from the inner tube (5). The resulting dimensions at the distal end of the outer tube (20) are an inside diameter of about 0.030–0.032 inch and an outside diameter of about 0.034–0.036 inch.

Figure 3:
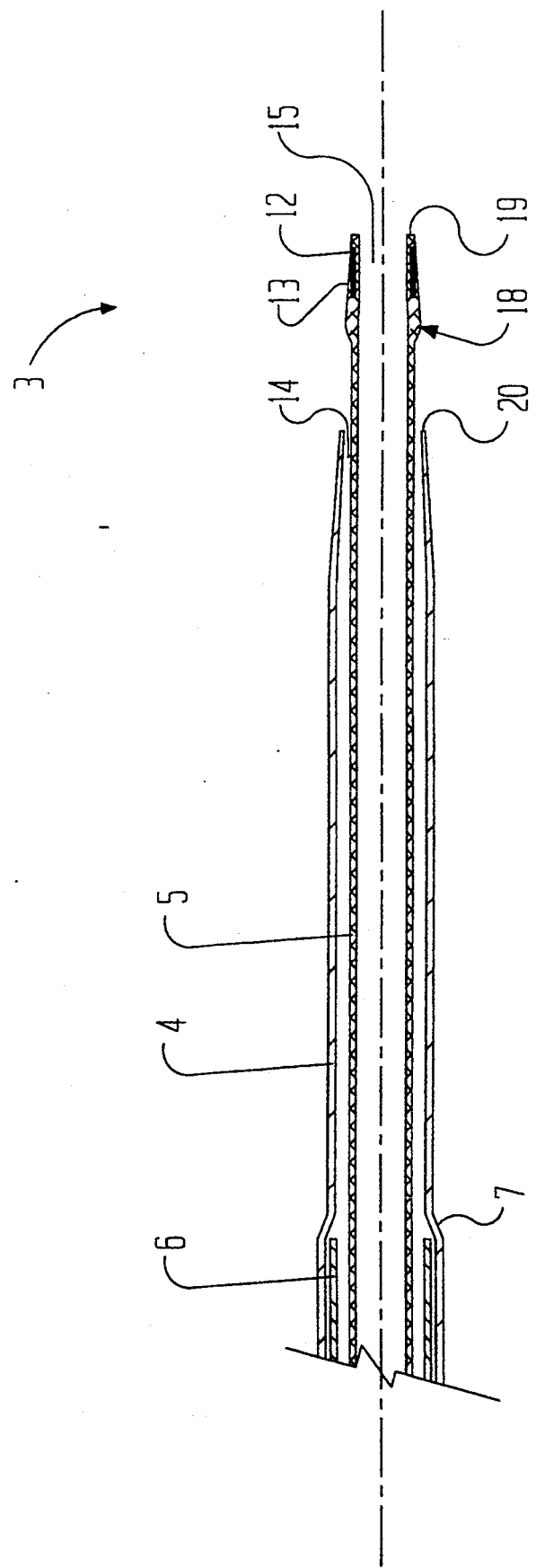
FIG. 3 is a detailed cross-sectioned side view of the distal portion of another preferred embodiment of the present invention.

Referring now to FIG. 3, an alternate preferred embodiment of the distal end of the device (3) is shown with an enlarged head (18) on the inner tube (5). The marker band (12) is loaded and secured to the inner tube (5) just as the embodiment in FIG. 2. The enlarged head (18) is formed by pushing the inner tube (19) into a heated die which bulks up material just proximal and distal to the marker band (12). This creates a ledge on either side of the marker band as with the embodiment in FIG. 2 but to a greater extent. Adhesive potting (13) is used to secure the marker band (12) and provide a smooth transition over the marker band (12). The resulting dimensions of the enlarged head (18) are an inside diameter of about 0.0185–0.0195 inch, a maximum outside diameter of about 0.030–0.032 inch and a length of about 1 mm. The dimensions of the distal portion of the outer tube (20) and the enlarged head (18) provide a smooth transition between the two members. The proximal end of the enlarged head (18) is located adjacent to the distal end of the outer tube (20) such that the inner tube (5) may be displaced proximally to engage the distal end of the outer tube (20). When the enlarged head (18) engages the distal end of the outer tube (20), additional column strength is provided to the inner tube (5) which facilitates improved support to the guide member (not shown). The enlarged head (18) does not occlude the infusion lumen (14) when the inner tube (5) is in its relaxed state. If the enlarged head (18) engages the distal end of the outer tube (20), fluid can be injected through the infusion lumen (14) to force the enlarged head (18) distally and thus advance the inner tube (5).

Figure 5:
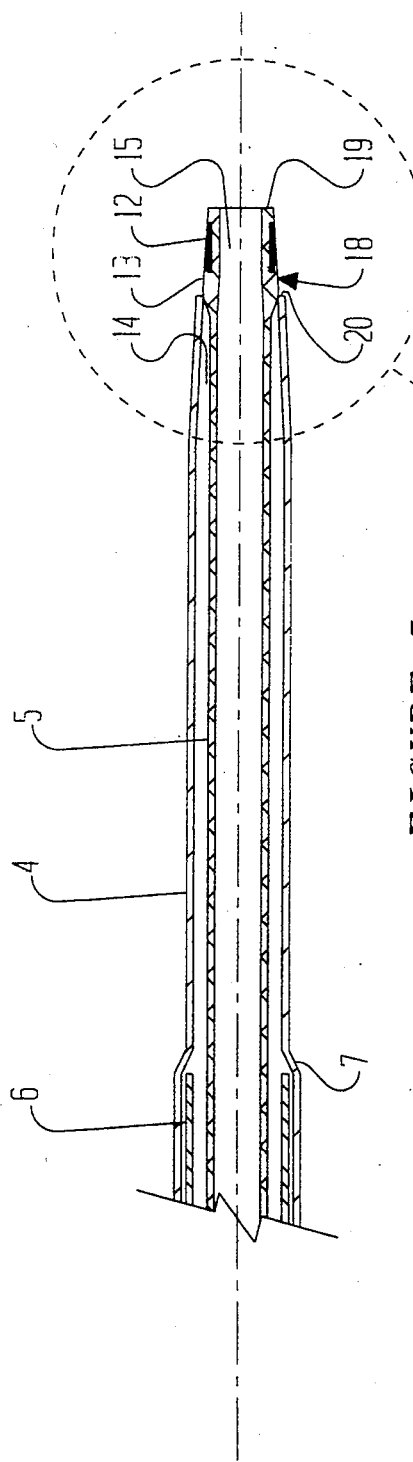
FIG. 5 is a detailed cross-section side view of the distal portion (shown engaged) of the embodiment shown in FIG. 3.
Figure 6:
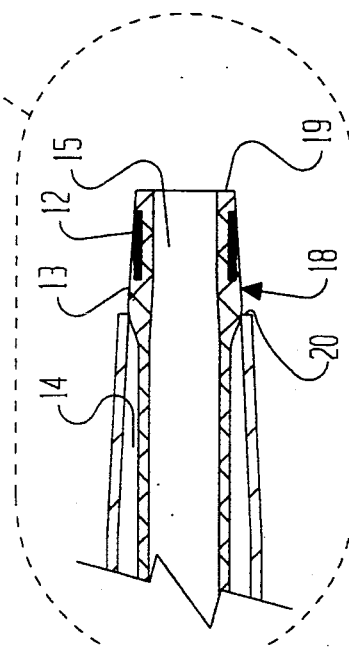
FIG. 6 is an enlarged detail view of the extreme distal portion of the embodiment shown in FIG. 5.

As shown in FIGS. 5 and 6, the distal end of the inner tube (5) extends distally beyond the distal end (20) of the outer tube (4). The enlarged head (18) on the inner tube (5) may engage the distal end (20) of the outer tube (4) so as to limit longitudinal movement and transmit longitudinal force from the outer tube (4) to the inner tube (5).

Figure 4:
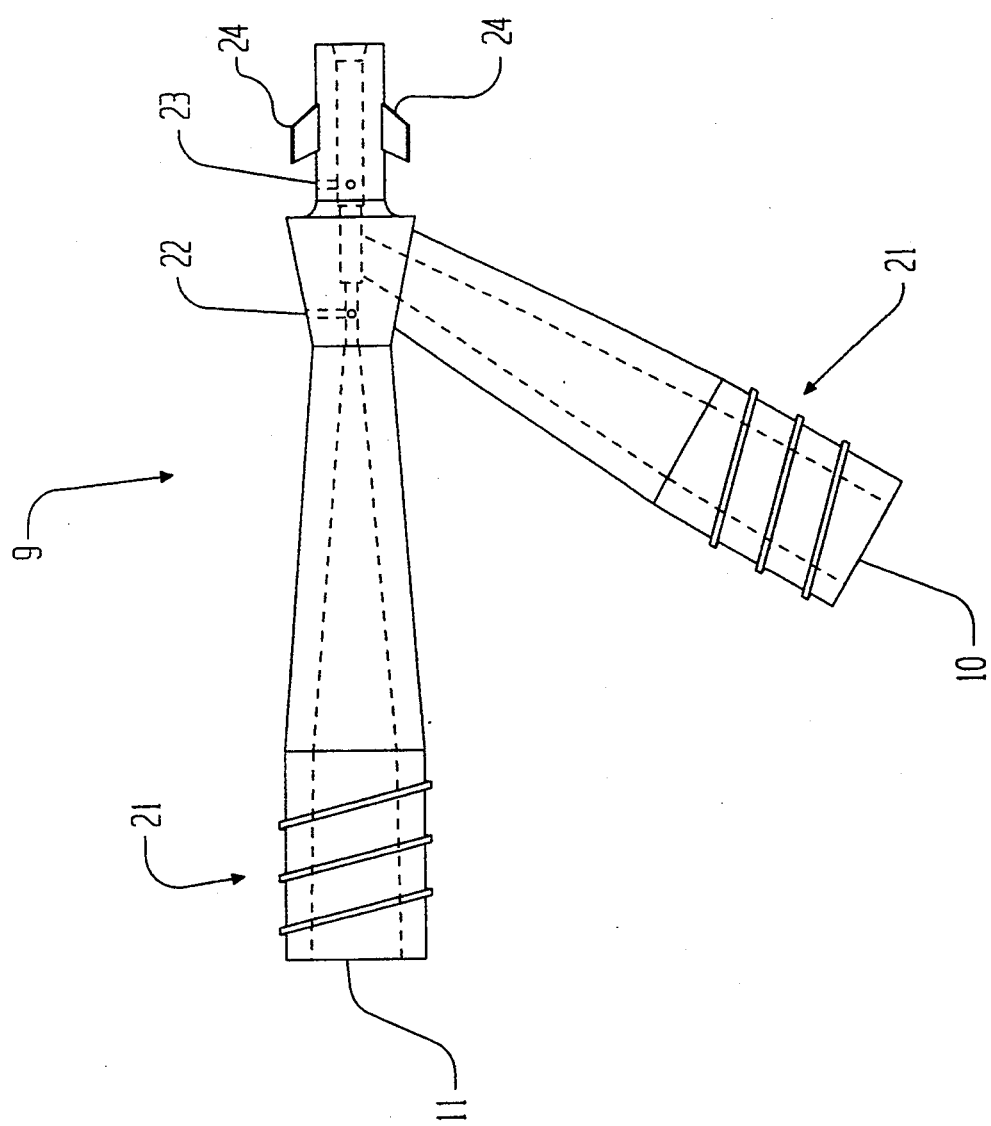
FIG. 4 is a detailed side view of the preferred manifold of the present invention.

Referring now to FIG. 4, the preferred manifold (9) is shown. Any manifold adapted for two independent lumen type devices can be used. For example, the manifold described in Robinson et al U.S. Pat. No. 4,838,269, herein incorporated by reference, may be utilized. The manifold (9) in FIG. 4 is unique in so far as it is made of only one injection molded part and is adapted to be adhesively secured to two coaxial tubes. The manifold (9) includes an infusion port (10) a guide port (11) and a fitting (21) connected to each port. The fitting (21) may be a luer fitting (shown), a homeostatic fitting, or a compression fitting. The fittings are adapted to receive conventional medical accessories such as a syringe, Y-adapter, medical tubing, another luer/compression/homeostatic fitting, and the like. The manifold (9) is secured to the inner tube (5) and the outer tube (4) by inserting the inner tube (5) to extend just beyond the adhesive injection port (22) and inserting the outer tube (4) to extend just beyond the adhesive injection port (23) but not beyond the infusion port (10). When the tubes are in place, an adhesive, such as a UV (ultra violet radiation) curable adhesive, is injected into both adhesive injection ports (22,23). If required, the manifold is exposed to sufficient UV radiation to cure the adhesive. The manifold is preferably made of a relatively transparent polycarbonate to allow for UV radiation to pass through to the bond sites. The manifold also includes flanges (24) which are adapted to receive a strain relief tube (not shown). The strain relief tube provides a smooth transition from the relatively stiff manifold to the relatively flexible shaft and thus prevents the device (1) from kinking just distal to the manifold (9). The strain relief tube is about 1.0–3.0 inches long and is of sufficient inside diameter to fit over the distal portion of the manifold and the proximal portion of the outer tube (4). The flanges allow for a strain relief to be attached without the use of adhesives. The single injection molded part design of the manifold (9) reduces part costs, reduces assembly costs, and reduces the probability of scrap due to poor adhesive bonds.

Referring back to FIG. 1, the construction of the device (1) provides a lumen specifically adapted to receive a guide member. The design of the guide lumen can be made to provide guide member support, specifically support of the distal end of the guide member. This is significant because guide members often have atraumatic tips which easily buckle when encountered by a vascular obstruction or occlusion. The guide lumen of the present invention can be sized to receive a guide member such that the clearance between the guide member and the inside diameter of the guide lumen is sufficiently small so as to inhibit buckling of the guide member while allowing relatively free guide member movement. This feature can also serve to effect the curvature of the distal tip of the guide member. For example, a curved tip of a guide member may be selectively straightened by advancing the device (1) over the guide member. By effecting the curvature of the distal tip of the guide member, the treating physician can more precisely navigate the guide member through tortuous vascular pathways and probe for a pathway through a tight occlusion.

The device (1) also has the ability to inject fluids in a lumen other than the guide member lumen. This is significant for several reasons. For example, this feature negates the need for a seal about the guide member in order to infuse fluids. Also, this feature prevents contrast media from inhibiting guide member movement when the contrast media becomes exposed to air and becomes prone to adhesion.

The device (1) also has the ability to visualize the vascular pathway both locally and broadly, and to manipulate the guide member, all independently. Specifically, the following three steps can be done independently and/or simultaneously. First, contrast media can be injected into the guide catheter and around the navigation and visualization assist device to visualize the vascular pathway broadly or adjacent to and distal from the ostium of the coronary artery. Second, contrast media can be injected into the navigation and visualization assist device to visualize the vascular pathway locally or adjacent the distal end of the advanced guide member. This feature may be used to determine if the guide member has followed the desired path or followed an incorrect path such as a sub-intimal path. And third, the guide member can be manipulated to advance along the desired vascular pathway. The ability to perform these steps independently allows the treating physician a significant amount of freedom to access difficult vascular pathways and cross difficult occlusions.

The device (1) also has the ability to locally infuse thrombolytic agents to aid breaking up occlusive material while simultaneously manipulating the guide member. Thus the treating physician can create a path across an occlusion by both manipulating a guide member and breaking up the occlusion with localized drug infusions.

The device (1) also has other capabilities which can be appreciated with thorough review of the preceding specification and drawings. Workers skilled in the art will recognize that changes can be made to the embodiments described herein, including, but not limited to, changes in structure, manufacture, and use without departing from the spirit or scope of the present invention.

The following is claimed:

1. An intravascular device for use in combination with a guide wire and a guide catheter, the device comprising:

an elongate shaft with an exterior, a proximal end and a distal end, the elongate shaft including an inner tube defining a proximal end, a distal end and a first lumen, the shaft further including an outer tube defining a proximal end and a distal end, the outer tube disposed about the inner tube defining a second annular lumen therebetween, the second lumen being in fluid communication with the exterior of the shaft through a distal face opening, the distal end of the inner tube extending distally beyond the distal end of the outer tube., the distal end of the inner tube engaging the distal end of the outer tube so as to limit relative longitudinal movement and transmit longitudinal force from the outer tube to the inner tube;

a first fitting connected to the proximal end of the elongate shaft, the first fitting being in fluid communication with the first lumen; and a second fitting connected to the proximal end of the elongate shaft, the second fitting being in fluid communication with the second lumen.

* * * * *